(12) United States Patent
Bitar et al.

(10) Patent No.: US 10,709,849 B2
(45) Date of Patent: Jul. 14, 2020

(54) GUIDE FOR AN INJECTION DEVICE

(71) Applicant: Cilag GmbH International, Zug (CH)

(72) Inventors: Ahmad Bitar, Cambridgeshire (GB); Douglas Ivan Jennings, Hertfordshire (GB)

(73) Assignee: Cilag GmbH International, Zug (CH)

( * ) Notice: Subject to any disclaimer, the term of this patent is extended or adjusted under 35 U.S.C. 154(b) by 695 days.

(21) Appl. No.: 14/897,400

(22) PCT Filed: Jun. 11, 2014

(86) PCT No.: PCT/EP2014/062160
§ 371 (c)(1),
(2) Date: Dec. 10, 2015

(87) PCT Pub. No.: WO2014/198791
PCT Pub. Date: Dec. 18, 2014

(65) Prior Publication Data
US 2016/0106930 A1    Apr. 21, 2016

(30) Foreign Application Priority Data

Jun. 11, 2013 (GB) .................... 1310372.6

(51) Int. Cl.
*A61M 5/32* (2006.01)
*A61M 5/20* (2006.01)
*A61M 5/42* (2006.01)

(52) U.S. Cl.
CPC ........ *A61M 5/3287* (2013.01); *A61M 5/2033* (2013.01); *A61M 5/3202* (2013.01);
(Continued)

(58) Field of Classification Search
CPC .............. A61M 5/3287; A61M 5/2033; A61M 5/3202; A61M 5/425; A61M 2005/2006;
(Continued)

(56) References Cited

U.S. PATENT DOCUMENTS 1,845,036 A   2/1932   Busher
2,019,382 A   10/1935  Aronson
(Continued)

FOREIGN PATENT DOCUMENTS

CA   2445511 A1   11/2002
CH   518102 A   1/1972
(Continued)

OTHER PUBLICATIONS

International Search Report dated Jul. 9, 2004; International Application No. PCT/GB03/05494.
(Continued)

*Primary Examiner* — Laura A Bouchelle
*Assistant Examiner* — John A Doubrava
(74) *Attorney, Agent, or Firm* — Steven J. Schwarz

(57) ABSTRACT

There is provided a guide 200 for contacting an injection device 110 with a user; the guide 200 having a first end 210 adapted to engage a housing 112 of the injection device 110 and a second end 220 adapted to engage the surface of a user's skin, wherein the guide 200 permits movement of the housing 112 towards the user's skin.

20 Claims, 3 Drawing Sheets

(52) U.S. Cl.
CPC ..... *A61M 5/425* (2013.01); *A61M 2005/2006* (2013.01); *A61M 2005/206* (2013.01); *A61M 2005/208* (2013.01); *A61M 2005/2073* (2013.01)

(58) Field of Classification Search
CPC .... A61M 2005/206; A61M 2005/2073; A61M 2005/208; A61M 2005/2013; A61M 2005/42; A61M 2005/46
USPC ........................................................ 604/115
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,752,918 A | 7/1956 | Rooseboom |
| 2,764,977 A | 10/1956 | Ferguson |
| 2,828,742 A | 4/1958 | Ashkenaz |
| 2,845,065 A * | 7/1958 | Gabriel ............... A61M 5/3243 604/198 |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Ben Moura |
| 3,674,033 A * | 7/1972 | Powers ................. A61M 25/02 604/264 |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,373,526 A * | 2/1983 | Kling ..................... A61M 5/46 604/117 |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,500,310 A | 2/1985 | Christinger |
| 4,507,118 A | 3/1985 | Dent |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,695,274 A | 9/1987 | Fox |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,073,170 A | 12/1991 | Schneider |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,188,613 A | 2/1993 | Shaw |
| 5,190,526 A | 3/1993 | Murray et al. |
| 5,242,400 A | 9/1993 | Blake et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,385,551 A | 1/1995 | Shaw |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,634,906 A * | 6/1997 | Haber ................... A61M 5/326 604/136 |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |

(56) References Cited

U.S. PATENT DOCUMENTS

| | | |
|---|---|---|
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,891,086 A | 4/1999 | Terrence et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,989,229 A | 11/1999 | Chiappetta |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart |
| 6,209,738 B1 | 4/2001 | Jansen et al. |
| 6,221,044 B1 | 4/2001 | Grecco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| RE37,439 E | 11/2001 | Firth et al. |
| 6,317,939 B1 | 11/2001 | Malin |
| 6,330,960 B1 | 12/2001 | Faughey et al. |
| 6,332,875 B2 * | 12/2001 | Inkpen ............... A61M 5/3287 604/117 |
| 6,371,939 B2 | 4/2002 | Bergens et al. |
| 6,371,959 B1 | 4/2002 | Trice |
| 6,387,078 B1 | 5/2002 | Gillespie |
| 6,391,003 B1 | 5/2002 | Lesch |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,536,723 B1 | 3/2003 | Nakatani |
| 6,537,252 B1 | 3/2003 | Hansen |
| 6,544,234 B1 | 4/2003 | Gabriel |
| 6,565,540 B2 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landua |
| 6,575,939 B1 | 6/2003 | Brunel |
| 6,579,269 B1 | 6/2003 | Kleyman |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landua |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 | 6/2004 | Arnissolle |
| 6,767,336 B1 | 7/2004 | Kaplan |
| 6,770,056 B2 | 8/2004 | Price et al. |
| 6,776,777 B2 | 8/2004 | Barelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,155 B2 | 3/2010 | Raven et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,785,292 B2 | 8/2010 | Harrison |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |

(56) References Cited

U.S. PATENT DOCUMENTS

| | | |
|---|---|---|
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,317,751 B2 | 11/2012 | Alheidt |
| 8,343,110 B2 | 1/2013 | Burnell |
| 8,409,138 B2 | 4/2013 | James et al. |
| 8,409,141 B2 | 4/2013 | Johansen et al. |
| 8,491,530 B2 | 7/2013 | Maritan |
| 8,556,861 B2 | 10/2013 | Tsals |
| 8,696,628 B2 | 4/2014 | Grunhut |
| 8,932,264 B2 | 1/2015 | DeSalvo |
| 8,968,236 B2 | 3/2015 | Jennings et al. |
| 9,028,451 B2 | 5/2015 | Jennings |
| 9,248,245 B2 | 2/2016 | Ekman et al. |
| 9,314,574 B2 | 4/2016 | Roberts et al. |
| 9,358,346 B2 | 6/2016 | Beyeler |
| 9,592,350 B2 | 3/2017 | Roberts et al. |
| 9,675,757 B2 | 6/2017 | Harrison |
| 9,757,520 B2 | 9/2017 | Corrigan |
| 2001/0005781 A1 | 6/2001 | Bergens et al. |
| 2001/0021826 A1 | 9/2001 | Fisher et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0039394 A1 | 11/2001 | Terrence et al. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0187405 A1 | 10/2003 | Gatti |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1* | 12/2003 | Tsals ............... A61M 5/20 604/116 |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2004/0254526 A1 | 12/2004 | Terrence et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0165360 A1 | 7/2005 | Stamp |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0021716 A1 | 1/2007 | Hansen |
| 2007/0027430 A1 | 2/2007 | Hommann |

(56) References Cited

U.S. PATENT DOCUMENTS

| | | |
|---|---|---|
| 2007/0032775 A1 | 2/2007 | Niedospial et al. |
| 2007/0066939 A1 | 3/2007 | Krulevitch et al. |
| 2007/0078382 A1 | 4/2007 | Hommann et al. |
| 2007/0078428 A1 | 4/2007 | Reynolds et al. |
| 2007/0118094 A1 | 5/2007 | Bingham et al. |
| 2007/0135767 A1 | 6/2007 | Gillespie, II et al. |
| 2007/0142787 A1 | 6/2007 | Scherer |
| 2007/0150842 A1 | 6/2007 | Chaudhri et al. |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2007/0244456 A1 | 10/2007 | Fangrow |
| 2007/0244457 A1 | 10/2007 | Fangrow |
| 2007/0244458 A1 | 10/2007 | Fangrow |
| 2007/0244459 A1 | 10/2007 | Fangrow |
| 2007/0244460 A1 | 10/2007 | Fangrow |
| 2007/0244461 A1 | 10/2007 | Fangrow |
| 2007/0244462 A1 | 10/2007 | Fangrow |
| 2007/0244463 A1 | 10/2007 | Warren et al. |
| 2007/0244464 A1 | 10/2007 | Fangrow et al. |
| 2007/0244465 A1 | 10/2007 | Fangrow |
| 2007/0244466 A1 | 10/2007 | Fangrow |
| 2008/0033395 A1 | 2/2008 | Alchas |
| 2008/0071225 A1 | 3/2008 | Hommann et al. |
| 2008/0154192 A1 | 6/2008 | Schraga |
| 2008/0161770 A1 | 7/2008 | Fangrow |
| 2008/0172001 A1 | 7/2008 | Reynolds et al. |
| 2008/0172024 A1 | 7/2008 | Yow |
| 2008/0213590 A1 | 9/2008 | Greiner et al. |
| 2008/0249462 A1 | 10/2008 | Nilufer et al. |
| 2008/0249498 A1 | 10/2008 | Fangrow |
| 2008/0262427 A1 | 10/2008 | Hommann |
| 2008/0269680 A1 | 10/2008 | Ibranyan et al. |
| 2008/0306443 A1 | 12/2008 | Neer et al. |
| 2008/0312592 A1 | 12/2008 | Barrow-Williams et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0149812 A1 | 6/2009 | MacAulay |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0049125 A1 | 2/2010 | James et al. |
| 2010/0063444 A1 | 3/2010 | Wikner |
| 2010/0234811 A1 | 9/2010 | Schubert et al. |
| 2010/0286714 A1 | 11/2010 | Gyrn et al. |
| 2011/0092954 A1 | 4/2011 | Jennings |
| 2011/0098647 A1 | 4/2011 | Jennings |
| 2011/0098655 A1 | 4/2011 | Jennings et al. |
| 2011/0098656 A1* | 4/2011 | Burnell ............... A61M 5/2033 604/198 |
| 2011/0130743 A1 | 6/2011 | Jennings et al. |
| 2011/0144594 A1 | 6/2011 | Sund et al. |
| 2011/0172640 A1 | 7/2011 | Cronenberg et al. |
| 2011/0245761 A1 | 10/2011 | Dean et al. |
| 2011/0282278 A1 | 11/2011 | Stamp et al. |
| 2012/0046615 A1 | 2/2012 | Iwase et al. |
| 2012/0232491 A1 | 9/2012 | Jennings |
| 2012/0283698 A1 | 11/2012 | Millerd |
| 2012/0323177 A1 | 12/2012 | Adams et al. |
| 2013/0046246 A1 | 2/2013 | Boyd et al. |
| 2013/0060232 A1 | 3/2013 | Adlon et al. |
| 2013/0096512 A1 | 4/2013 | Ekman et al. |
| 2013/0125441 A1 | 5/2013 | Westwood et al. |
| 2013/0150801 A1 | 6/2013 | Barrow-Williams et al. |
| 2013/0267898 A1 | 10/2013 | Hourmand et al. |
| 2013/0310759 A1 | 11/2013 | Barrow-Williams et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0221974 A1 | 8/2014 | Bechmann et al. |
| 2014/0257185 A1 | 9/2014 | Bechmann et al. |
| 2014/0257193 A1 | 9/2014 | Bostrom et al. |
| 2015/0025458 A1* | 1/2015 | Heald ............... A61M 5/3287 604/115 |
| 2015/0190590 A1 | 7/2015 | Macarthur et al. |
| 2018/0312590 A1 | 11/2018 | Cogswell et al. |

FOREIGN PATENT DOCUMENTS

| | | |
|---|---|---|
| CH | 703993 | 3/2012 |
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 387465 | 1/1924 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 2/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 11/2003 |
| EP | 0096314 A2 | 12/1983 |
| EP | 0144625 A2 | 6/1985 |
| EP | 0240787 A2 | 10/1987 |
| EP | 0338806 A2 | 10/1989 |
| EP | 0515473 B1 | 12/1992 |
| EP | 0518416 A1 | 12/1992 |
| EP | 0331452 B1 | 8/1993 |
| EP | 0585626 A1 | 3/1994 |
| EP | 0389938 B1 | 5/1994 |
| EP | 0516473 B1 | 2/1996 |
| EP | 0111724 B1 | 2/1998 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1586341 B1 | 1/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 1932558 B1 | 6/2011 |
| EP | 1755710 B1 | 3/2012 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2319560 | 5/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2268342 | 9/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |

(56) References Cited

FOREIGN PATENT DOCUMENTS

| | | |
|---|---|---|
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 A | 5/1920 |
| GB | 412054 A | 6/1934 |
| GB | 728248 A | 4/1955 |
| GB | 909898 A | 11/1962 |
| GB | 1263355 A | 2/1972 |
| GB | 1311937 A | 3/1973 |
| GB | 1514725 A | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 30-001091 | 1/1930 |
| JP | 49-77487 | 7/1974 |
| JP | 49-021036 | 6/1979 |
| JP | 54-087694 | 1/1982 |
| JP | 59-115053 A | 7/1984 |
| JP | 2-185261 A | 7/1990 |
| JP | 2-502971 T | 9/1990 |
| JP | H 02-299660 A | 12/1990 |
| JP | 03-129156 | 12/1991 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-065786 | 3/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-154005 | 5/2003 |
| JP | 2003-284776 | 10/2003 |
| JP | 2003-532500 T | 11/2003 |
| JP | 2003-533288 A | 11/2003 |
| JP | 2004-033737 A | 2/2004 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2005-534433 | 11/2005 |
| JP | 2006-223858 A | 8/2006 |
| JP | 2007-207611 A | 8/2007 |
| JP | 2008-284177 A | 11/2008 |
| JP | 2008-295590 | 12/2008 |
| JP | 2008-543500 | 12/2008 |
| JP | 2012-503995 | 2/2012 |
| JP | 2013-529527 | 7/2013 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 A1 | 11/1988 |
| WO | WO 1988/10129 A1 | 12/1988 |
| WO | WO 92/19296 A | 11/1992 |
| WO | WO 1993/02186 A1 | 2/1993 |
| WO | WO 93/21986 A2 | 11/1993 |
| WO | WO 1993/23098 A1 | 11/1993 |
| WO | WO 1994/04207 A1 | 3/1994 |
| WO | WO 94/07554 A1 | 4/1994 |
| WO | WO 94/11041 A1 | 5/1994 |
| WO | WO 94/13342 A1 | 6/1994 |
| WO | WO 94/013343 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/31235 A1 | 11/1995 |
| WO | WO 1995/29720 A1 | 11/1995 |
| WO | WO 1995/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 1997/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 1999/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 A1 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/077384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |

(56) References Cited

FOREIGN PATENT DOCUMENTS

| | | |
|---|---|---|
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 A1 | 11/2003 |
| WO | WO 03/097133 A1 | 11/2003 |
| WO | WO 03/099358 A2 | 12/2003 |
| WO | WO 04/007554 A1 | 1/2004 |
| WO | WO 04/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 | 10/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/044348 | 5/2005 |
| WO | WO 2005/056077 | 6/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/059233 A1 | 5/2008 |
| WO | WO 2008/075033 A | 6/2008 |
| WO | WO 2008/093063 A2 | 8/2008 |
| WO | WO 2010/023303 A1 | 3/2010 |
| WO | WO 2010/056712 | 5/2010 |
| WO | WO 2011/117283 | 9/2011 |
| WO | WO 2012/000835 A1 | 1/2012 |
| WO | WO 2012/059517 | 5/2012 |
| WO | WO 2012/093071 | 7/2012 |
| WO | WO 2012/140088 | 10/2012 |
| WO | WO 2012/155035 | 11/2012 |
| WO | WO 2013/070715 | 5/2013 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
International Search Report dated Sep. 5, 2005; International Application No. PCT/GB2005/002131.
International Search Report dated Sep. 9, 2005; International Application No. PCT/GB2005/002120.
International Search Report dated Sep. 5, 2005; International Application No. PCT/GB2005/002137.
International Search Report dated Sep. 6, 2005; International Application No. PCT/GB2005/002108.
International Search Report dated Sep. 5, 2005; International Application No. PCT/GB2005/002105.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Oct. 9, 2007; International Application No. PCT/GB2006/001023.
International Search Report dated Feb. 27, 2007; International Application No. PCT/IB2006/002792.
International Search Report dated Aug. 22, 2007; International Application No. PCT/GB2007/001992.
International Search Report dated Sep. 4, 2007; International Application No. PCT/GB2007/002002.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
International Search Report dated Oct. 14, 2008; International Application No. PCT/GB2008/002580.
International Search Report dated Nov. 27, 2008; International Application No. PCT/GB2008/002579.
International Search Report dated Oct. 10, 2008; International Application No. PCT/GB2008/002573.

(56) References Cited

OTHER PUBLICATIONS

International Search Report dated Oct. 10, 2008; International Application No. PCT/GB2008/002583.
International Search Report dated Sep. 30, 2009; International Application No. PCT/GB2009/001447.
International Search Report dated Oct. 2, 2009; International Application No. PCT/GB2009/001448.
International Search Report dated Oct. 5, 2009; International Application No. PCT/GB2009/001451.
International Search Report dated Oct. 6, 2009; International Application No. PCT/GB2009/001453.
International Search Report dated Oct. 5, 2009; International Application No. PCT/GB2009/001445.
International Search Report dated Jan. 22, 2010; International Application No. PCT/GB2009/001446.
International Search Report dated Jan. 12, 2008; International Application No. PCT/GB2008/002475.
International Search Report dated Sep. 4, 2003; International Application No. PCT/GB03/01946.
International Search Report dated Sep. 8, 2014; International Application No. PCT/EP2014/062163.
International Search Report dated Sep. 8, 2014; International Application No. PCT/EP2014/062166.
International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
Page entitled 'Unusual cams' V. Ryan, 2002-2009; from www.technologystudent.com.
Cam Design and Manufacture; Preben W. Jensen; Industrial Press; New York; 1965; Chapter 1.
Definition of a cam taken from www.wikipedia.com, Feb. 7, 2012.
Farm gate latch image Website showing gate latches from Jun. 3, 2004, http://dictionary.cambridge.org/dictionary/british/latch.
Engineering Tolerance, definition, Aug. 15, 2013; http://en.wikipedia.org/wiki/Engineering_tolerance.
Witness statement statement by Mr. Jeremy Marshal, Head of Technology Development & CI of the opponent, Dec. 2, 2011.
Patient instruction leaflet Glaxo Mode d'emploi (FR); Referred to in Statement of Jeremy Marshall, Dec. 2, 2011.
Assembly instructions, process flow diagrams for AJ1200CE129 and AJ1200CA00 together with drawings for AJ501 all dated differently; starting in 1993 and the latest dates referring to 2002, Referred to in Statement of Jeremy Marshall, Dec. 2, 2011.
Discussion session at the 5th International Nurses' Workshop on Multiple Sclerosis.
Article from diabetes health, Feb. 1, 1997.
Parts list AJ503 Auto injector—Glaxo Jul. 29, 1992 (change 92-7-45)/ Oct. 18, 1993 with drawings dated between 1986 and 1991.
Photos of a sample, Referred to in Statement of Jeremy Marshall, Dec. 2, 2011.
Company's sales ledger for the period of Nov. 1991-May 1993.
510(k) pre-market notification Apr. 19, 1990.
Fax dated Jul. 21, 1995 Imigran injection launch data.
Patient instruction leaflet, Imigran, Referred to in Statement of Jeremy Marshall, Dec. 2, 2011.
Patient instruction leaflet Glaxo Neurologie (NL), Referred to in Statement of Jeremy Marshall, Dec. 2, 2011.
Parts list AJ501 stamped Aug. 6, 2002.
Patient instruction leaflet Imigran (EN), Referred to in Statement of Jeremy Marshall, Dec. 2, 2011.
Detailed view of the retainer component AJ613 dated Jun. 15, 1993 last amended Nov. 8, 1995.
Production drawing Nov. 18, 2003, Autoject2 fixed needle AJ-0530-00-00-33.
Bill of material amendments log, Dec. 2, 2011.
Internet archive pages dated Dec. 4, 1999_1.
Internet archive pages dated Dec. 4, 1999_2.
Invoices of sales Dec. 12, 2005 Autoject 2—Product code AJ1300EA000 and invoice of sales Mar. 21, 2006 Autoject 2—Product code AJ1311EA000.
Hospital price list Mar. 1990 and pharmacy trade price list Mar. 1994 losing an Autoinjector AJ1200.
Production record of Feb. 15, 2001 referring to device part AJ501 and a packaged part No. AJ1200CA00, dated Feb. 15, 2001.
Production record, dated raised Feb. 15, 2001.
Parts list for AJ501, Referred to in Statement of Jeremy Marshall, Dec. 2, 2011.
General assembly drawing issued May 2, 1986, last amended Feb. 9, 1994.
Extracts from the company's sales ledger, Referred to in Statement of Jeremy Marshall, Dec. 2, 2011.
Extract from a medical shop catalogue, Referred to in Statement of Jeremy Marshall, Dec. 2, 2011.
Mechanical Engineer's Handbook; Dan B. Marghitu, J. David Irwin; Academic Press, Burlington, 2001.
Non-patent literature ISO 11040-4:1996('E').
European Pharmacopeia, 2002, p. 282-283.
"Starlock Fasteners": filed at the EPO by way of the opponent's letter of Apr. 3, 2013 and said to be retrieved from the website www.bakfin.com around that time.
Worksheet referred to in document A21; V. Ryan, 2002-2009; from www.technology student.com.
Dictionary definition of a latch; http://dictionary.cambridge.org/dictionary/british/latch, Oct. 12, 2014.
"Farm Gate Latch Image": filed at the EPO by way of the opponent's letter of Oct. 31, 2014.
GA drawing dated Jun. 10, 1994 several times amended.
Article Apr. 27, 2002 5th International Nurses' Workshop on Multiple Sclerosis.

\* cited by examiner

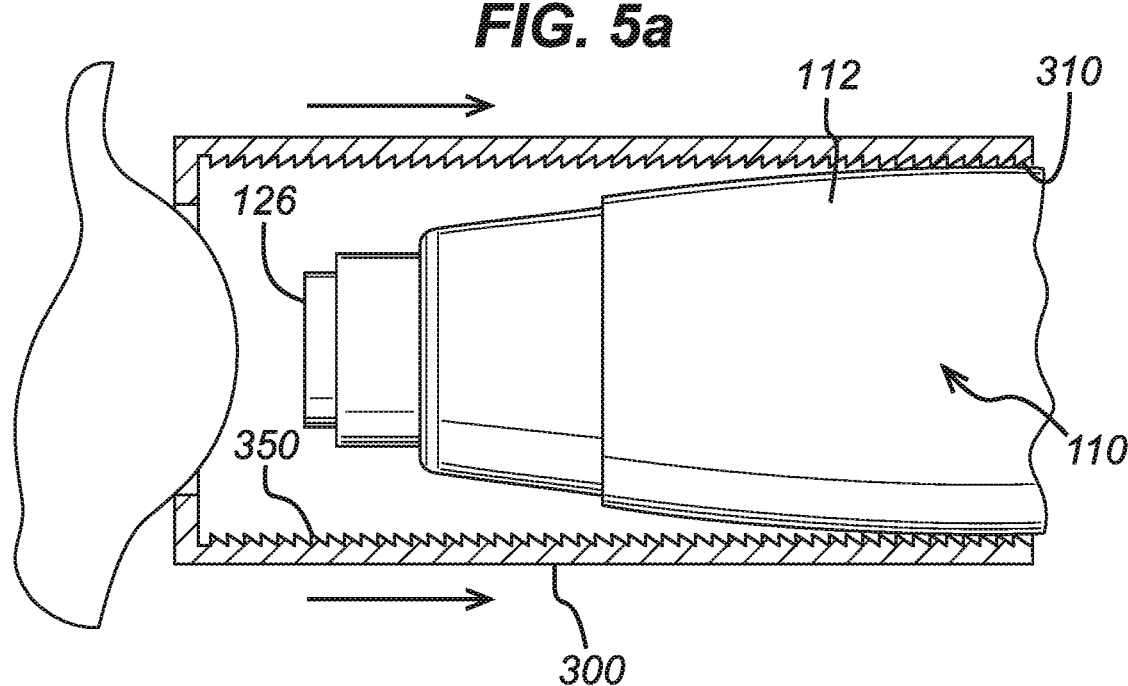
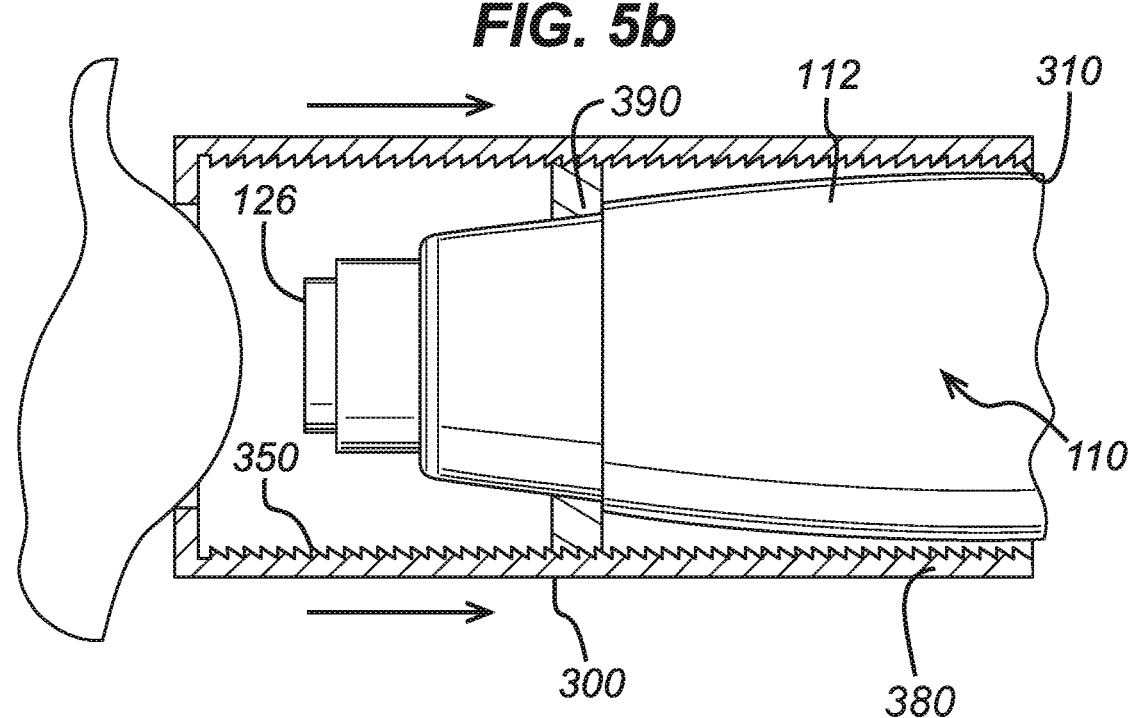

GUIDE FOR AN INJECTION DEVICE

FIELD OF THE INVENTION

The present invention relates to a guide for the housing of an injection device that receives a syringe, extends the syringe and discharges its contents, commonly known as an auto-injector and a kit comprising the injection device.

BACKGROUND OF THE INVENTION

Auto-injectors are known from WO 95/35126 and EP-A-0 516 473 and tend to employ a drive spring and some form of release mechanism that releases the syringe from the influence of the drive spring once its contents are supposed to have been discharged, to allow it to be retracted by a return spring.

An auto-injector is known from WO 2007/036676 which has a locking mechanism which must be disengaged before the release mechanism can be activated. In its locked position, the locking mechanism also prevents forward movement of the syringe out of the injection device against the bias of the return spring, for example when a cap gripping a boot covering the syringe needle, is removed. In the injection device described in WO 2007/036676, the locking mechanism comprises a sleeve which protrudes from an open end of the injection device. The sleeve is biased into its extended position by a resilient spring mechanism which must be overcome to disengage the locking mechanism. The locking mechanism can be disengaged by, for example, moving the sliding sleeve inwardly into the injection device. This can be done by forcing the end of the sliding sleeve against tissue and then activating the release mechanism.

It can be difficult for a user to position the sliding sleeve at the correct angle against the tissue and maintain it in that position as the locking mechanism is disengaged. Ensuring the sliding sleeve is forced against tissue at the correct angle and held sufficiently stable on the tissue as the locking mechanism is overcome is important to ensure reliable operation of the device as it is activated.

SUMMARY OF THE INVENTION

The injection device and kit of the present invention is designed to deal with the aforementioned problems.

In a first aspect of the invention, there is provided a guide for contacting an injection device with a user; the guide having a first end adapted to engage a housing of the injection device and a second end adapted to engage the surface of a user's skin, wherein the guide permits movement of the housing towards the user's skin.

The guide ensures that the housing moves towards the user's skin at the correct angle since it is engaged with the skin and directs the housing of the injection device towards it. It can be dimensioned for use with existing injection devices so that modification of the injection device is unnecessary. The guide could also be used to hold the auto-injector in position during long (high viscosity) or intramuscular injections.

The first end of the guide may be open. By 'open' it is meant that at least a portion of the injection device may pass through the first end.

This allows the guide to be placed on the skin and a discharge nozzle of the injection device to pass through it towards the user's skin.

The second end of the guide may be open, thereby providing a straightforward way for the user to insert the injection device into the guide. Again, by 'open' it is meant that at least a portion of the injection device may pass through the second end.

The guide may be cylindrical. Typically, injection devices are cylindrical, and so this shape of guide conforms well with most kinds of injection devices. A cylindrical guide is also found to be easily to grasp, and to be most comfortable when placed on the user's skin because it lacks sharp corners. Moreover, the shape provides a linear path for the injection device to travel down and holds the housing of the injection device securely. Of course, other shapes are also possible.

The guide may be flared towards the second end. The flared end stabilises the guide on the skin so that its position does not change as the housing is moved towards the skin.

The guide may be formed as a frame (rather than a solid tube structure, for example). In this case, the user can see the passage of the injection device towards the skin, which is found to be particularly reassuring since the user can anticipate when the injection device will contact the skin.

Alternatively, the guide may be formed with a continuous external surface. This provides a more secure guide since the user cannot access the distal end of the injection device as it is advanced towards the skin.

The guide may comprise at least one stabilising element at its second end which is adapted to project from the guide and stabilise the guide on the skin. This helps to improve the stability of the guide on the skin during use. In a preferred embodiment, the guide may comprise three stabilising elements at its second end. Additional stabilising elements provide additional stability to the guide on the skin.

The guide may comprise a first component and a second component moveable relative to the first component. The second component can be used to engage the housing and move it towards the skin while the first component remains fixed on the skin. In this way, the guide is capable of exerting some control over the progress of the injection device through the guide.

The second component may be adapted for indexed movement relative to the first component. This allows the user to more accurately control the movement of the injection device.

For example, the guide may further comprise a ratchet disposed on its inner surface such that the housing moves towards the user's skin incrementally. The ratchet may exist between the first and second components, or between the first component and the housing itself. This second arrangement allows the user to control the movement of the injection device without the need for a second component. In any case, the ratchet prevents the injection device being removed from the guide once it has been advanced towards the user's skin, which provides improved safety.

The second end may be configured to draw the user's skin up into the second end. For example, the second end may comprise an aperture of a particular shape which causes the skin therein to be pinched, and thus raised towards the distal end of the injection device. This configuration of the skin is advantageous for subcutaneous injections.

The second end may comprise a resilient portion which is biased inwards. This acts to pinch the skin together when the second end is placed on the skin. The resilient portion may comprise at least two resilient arms biased towards each other, which is particularly effective for pinching the skin together.

In a second aspect of the invention, there is provided a kit comprising the guide of any preceding embodiment and an automatic injection device having a housing.

The first end of the guide may be adapted to engage the housing at its distal end. The guide can be dimensioned to fit pre-existing injection devices ensuring that it is readily compatible.

The housing may have a first diameter and the first end may be dimensioned to surround the first diameter. The housing is then easily inserted into the first end of the housing. Preferably, the first end is dimensioned such that there is an interference fit between the housing and the guide.

The internal surface of the guide may be dimensioned to be in contacting juxtaposition with an external surface of the housing. This ensures that the housing remains aligned with the wall of the guide as the housing is advanced through the guide.

A portion of the housing may have a second diameter which is larger than the first diameter and the first end may be dimensioned to engage the portion of the housing having a second diameter. The second diameter portion prevents the housing being advanced towards the skin further than is necessary.

The second diameter portion may comprise a ridge, for example to act as a stop for the housing relative to the guide.

The first end may be integral to the housing of the injection device. Thus, the injection device and housing may be proved in one piece.

In a third aspect of the invention, there is provided an injection device comprising a housing adapted to receive a syringe having a discharge nozzle, the syringe being moveable in the housing on actuation of the injection device along a longitudinal axis from a retracted position in which the discharge nozzle is contained within the housing and an extended position in which the discharge nozzle of the syringe extends from the housing through an exit aperture at a distal end of the device, a sliding component which extends, when in a first position, from the aperture, and is movable towards the housing into a second, retracted, position; and a guide for contacting an injection device with a user; the guide having a first end adapted to engage the housing and a second end adapted to engage the surface of a user's skin, wherein the guide permits movement of the housing towards the user's skin.

The injection device may further comprise an actuator; and a drive adapted to be acted upon by the actuator and in turn act upon the syringe to advance it from its retracted position to its extended position and discharge its contents through the discharge nozzle.

The sliding component may be part of a locking mechanism moveable from an engaged position, when the sliding component is in its first position, to a disengaged position, when the sliding component is in its second position, and adapted to prevent actuation of the device when it is in its engaged position and permit actuation of the device when it is in its disengaged position.

The sliding sleeve can be moved into its disengaged position as the housing is moved against the skin. The guide ensures that the injection device is at the correct angle for this movement to take place.

The injection device or injection kit of any of the above embodiments may contain a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

By 'the injection device or injection kit may contain a substance' it is meant that the substance may be contained within a suitable medicament container, such as a vial or syringe, within the injection device, or within the syringe of the injection kit. Such medicament container may contain other substances, such as further active or inactive ingredients.

In a further aspect of the invention, a substance is provided, the substance being selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of said substance to a human subject using an injection device or injection kit according to any of the above embodiments.

In yet another aspect of the invention, an injection device is provided for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity, by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, to a human subject by using the injection device, where the injection device is an injection device or injection kit of any of the above embodiments.

By 'delivery of a substance' it is meant that the injection device is used to inject said substance into the human subject, for example by subcutaneous, intradermal or intramuscular injection. Said substance may be administered in combination with other substances, such as further active or inactive ingredients.

BRIEF DESCRIPTION OF THE DRAWINGS

The present invention will now be described with reference to the accompanying drawings, in which:

FIG. 5a shows a cross-section view of an alternative guide in accordance with the present invention;

FIG. 5b shows a cross-section view of an alternative guide in accordance with the present invention.

DETAILED DESCRIPTION OF THE DRAWINGS

Figure 1:
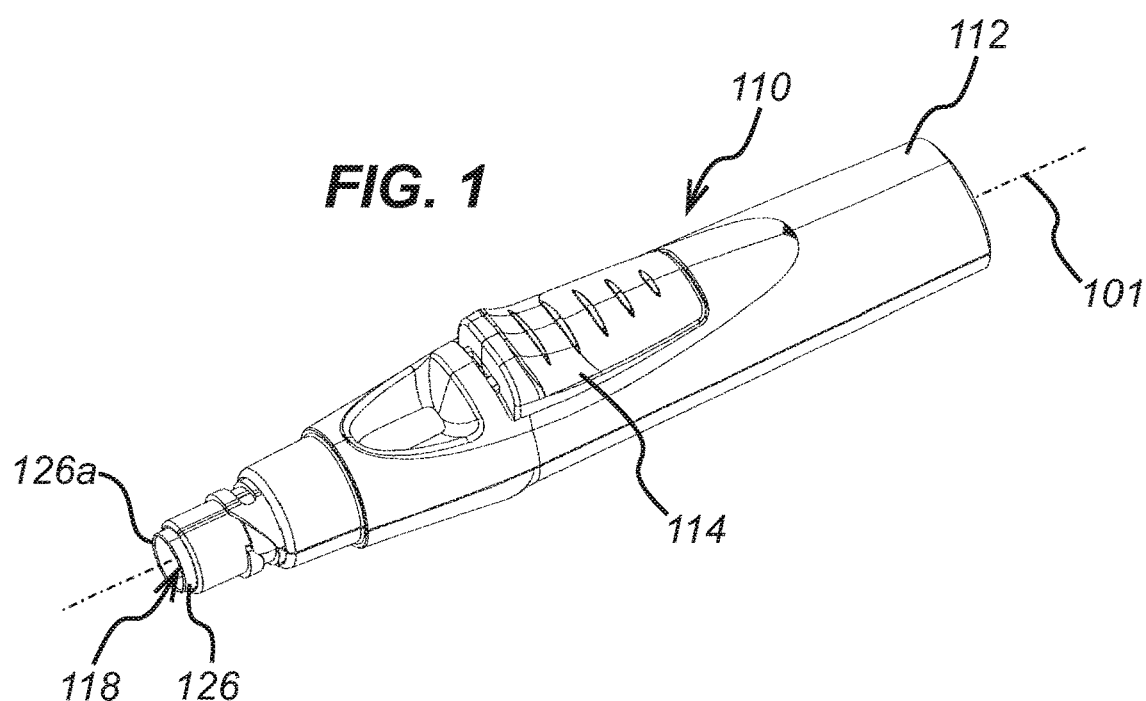
FIG. 1 shows a perspective view of an injection device having a locking mechanism including a sliding sleeve.
Figure 2:
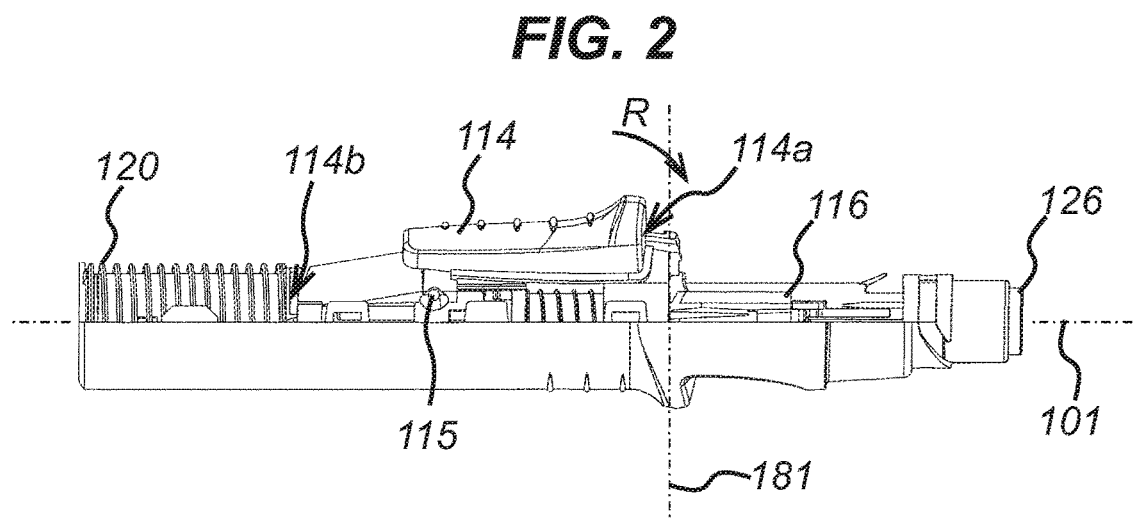
FIG. 2 shows a cutaway side view of an injection device having a locking mechanism including a sliding sleeve.
Figure 3:
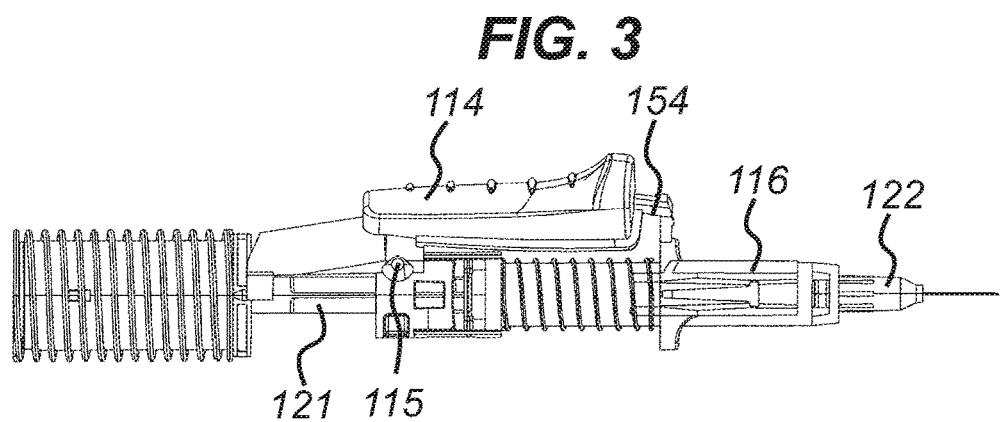
FIG. 3 show a side view of an injection device having a locking mechanism including a sliding sleeve.

FIGS. 1 to 3 show an injection device 110. The injection device 110 has an injection device housing 112 and a longitudinal axis 101.

A syringe (FIG. 3) is contained in the housing 112. The injection device 110 comprises trigger 114 (actuator) and a releasable locking mechanism 116. The trigger 114 has a first end 114a and a second end 114b. The trigger 114 is rotatable about a pivot 115 from a rest position (as shown in FIG. 2) to an active position. The second end 114b of the trigger 114 connects with a drive coupling 121 which is acted upon by a drive spring 120. The drive coupling 121 is in communication with the syringe 122.

Rotation of the trigger 114 about the pivot 115 in a direction R (i.e. downwards into the housing 112 at its first end 114a) causes the second end 114b of the trigger 114 to disengage from the drive coupling 121, thereby letting the drive spring 120 drive the syringe 122 (via the drive coupling 121) along the longitudinal axis 101 and out of an aperture 118 in the housing 112.

The releasable locking mechanism 116 is in communication with sliding sleeve 126 which protrudes, when in a first position, from the aperture 118 in the housing 112. The locking mechanism 116 is deactivated by movement of the sliding sleeve 126 along the longitudinal axis 101 into the housing 112 into a second position.

A first end 126a of the sliding sleeve 126 can be placed against a body into which drug is being delivered, thereby deactivating the releasable locking mechanism 116 and allowing the trigger 114 to rotate in direction R from its rest position to its active position.

The trigger 114 is provided at its first end 114a with a first portion having a cut-out. The first portion extends from the first end 114a of the trigger 114a in a direction substantially parallel to the longitudinal axis 101.

The releasable locking mechanism 116 includes a protrusion 154 which projects in a direction along a perpendicular axis 181 which is perpendicular to the longitudinal axis 101. The cut-out is dimensioned to receive the protrusion.

When the releasable locking mechanism 116 is in its first position, an end of the protrusion abuts an under-surface of the first portion 150, thereby preventing rotation of the trigger 114.

When the releasable locking mechanism 116 is in its second position (not shown) following movement of the sliding sleeve 126 into the housing 112, the cut-out is positioned above the end of the protrusion 154 allowing it to pass over the protrusion 154 when a downwards force is applied the trigger 114. Hence, the trigger 114 is no longer prevented from rotating and disengages itself from the drive coupling 121, thereby extending the syringe.

Figure 4A:
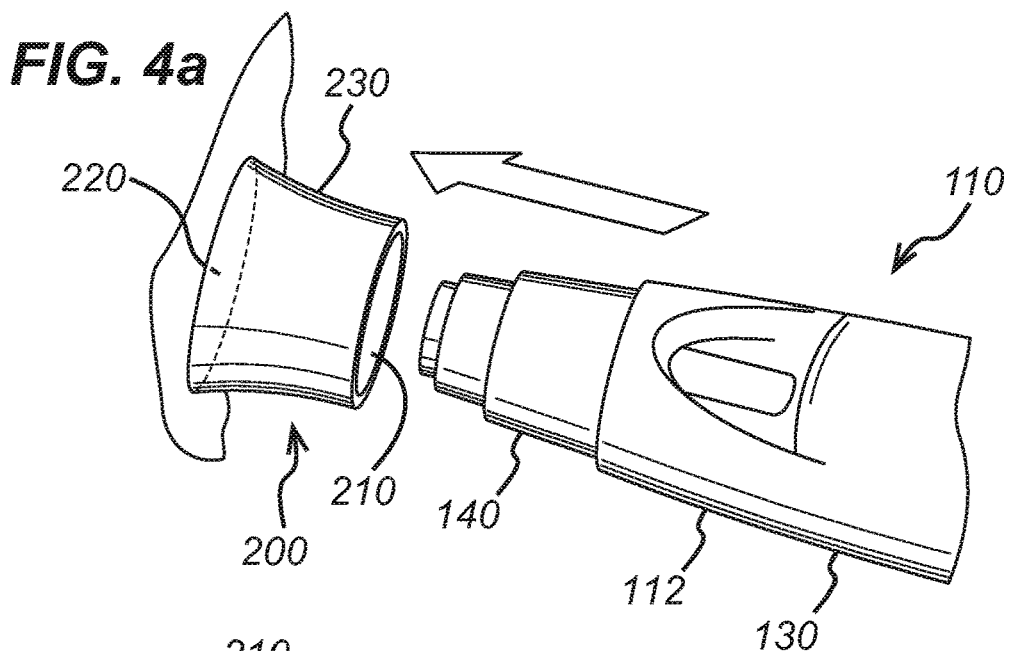
FIG. 4a shows a perspective view of a guide and an injection device of the present invention.
Figure 4B:
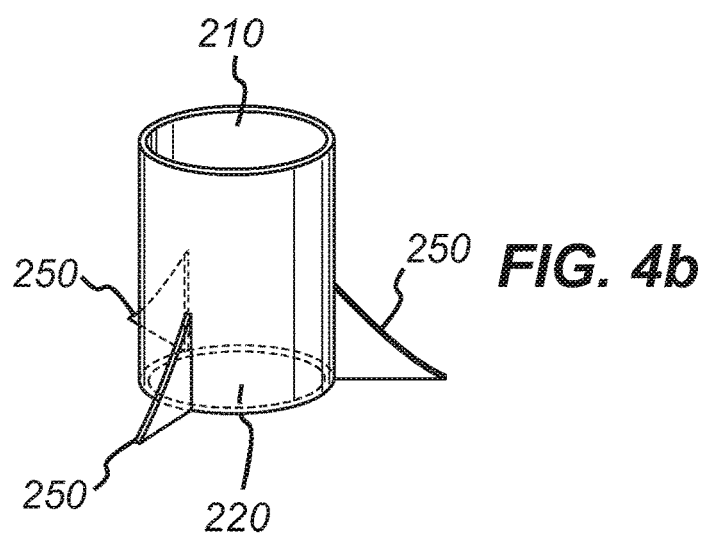
FIG. 4b shows a perspective view of an alternative guide in accordance with the present invention.

FIG. 4a shows a guide 200 in accordance with the present invention. The guide comprises a cylindrical portion which is open at both its first 210 end and second end 220. The guide is flared towards the second end. Alternatively, as shown in FIG. 4b, the second end 220 of the guide 200 may be cylindrical. The first end 210 is dimensioned to receive the housing 112 of an injection device such as the shown in FIGS. 1 to 3. The first end 210 of the guide 200 may be dimensioned such a first portion 130 of the housing 112 having a second diameter which is larger than a second portion 140 of the housing 112 cannot pass through the guide. The first portion engages the first end 210 of the housing 112 as the injection device is advanced through the guide 200. This provides a stop for the housing as it is advanced so that it cannot be pushed further against the skin than is necessary. Alternatively, a ridge may be provided on the housing 112 which engages the first end 210 of the guide 200 once the injection device 110 has been sufficiently advanced.

In use, the second end 220 of the guide 200 is attached to the user's skin as shown in FIG. 4a. The flared shape of the second end 220 acts to position the guide 200 at the correct angle to the user's skin and ensure that the guide is stable in this position. The injection device 110 is inserted into the first open end 210 of the guide. The guide 200 acts to direct the injection device 110 towards the user's skin at the correct angle such that when the sliding sleeve 126 contacts the user's skin, force is applied equally about its circumference and it is moved to its retracted position correctly, thereby enabling the user to actuate the injection device 110.

In FIG. 4a, the guide has a continuous external surface 230. Alternatively, the guide may be formed from a frame such that the user can see the movement of the sliding sleeve as the injection device is moved towards the skin.

As an alternative to the flared end, as shown in FIG. 4b, protrusions 250 may be provided at the second end 220 of the guide 200 which stabilise the guide 200 once it has been placed on the skin. The protrusions 250 may acts as tripod and prevent the guide tilting as the injection device is operated.

FIG. 5a shows an alternative embodiment of the guide 300, comprising a ratchet mechanism 350 on the inner surface of the guide. The ratchet 350 engages the surface of the housing 112 of the injection device 110 as it is inserted into the first open end 310 and moved towards the skin. The injection device 110 can then be moved incrementally towards the user's skin as the sliding sleeve 126 contacts the skin and moves from its extended to its retracted position. This allows the user to accurately judge how far the injection device 110 has been advanced. The injection device 110 can then not be removed from the guide 300, and thus the skin, once the locking mechanism has been deactivated.

Alternatively, as shown in FIG. 5b the ratchet mechanism may be a two-part mechanism, comprising a first moveable component 390 which engages the housing and moves with respect to the second component 380 of the guide in an indexed fashion. The first component 390 may be an annular component which engages the housing by a frictional fit. In another embodiment, not shown, the ratchet may be omitted such that the first component 390 may slide relative to the second component.

Figure 6:
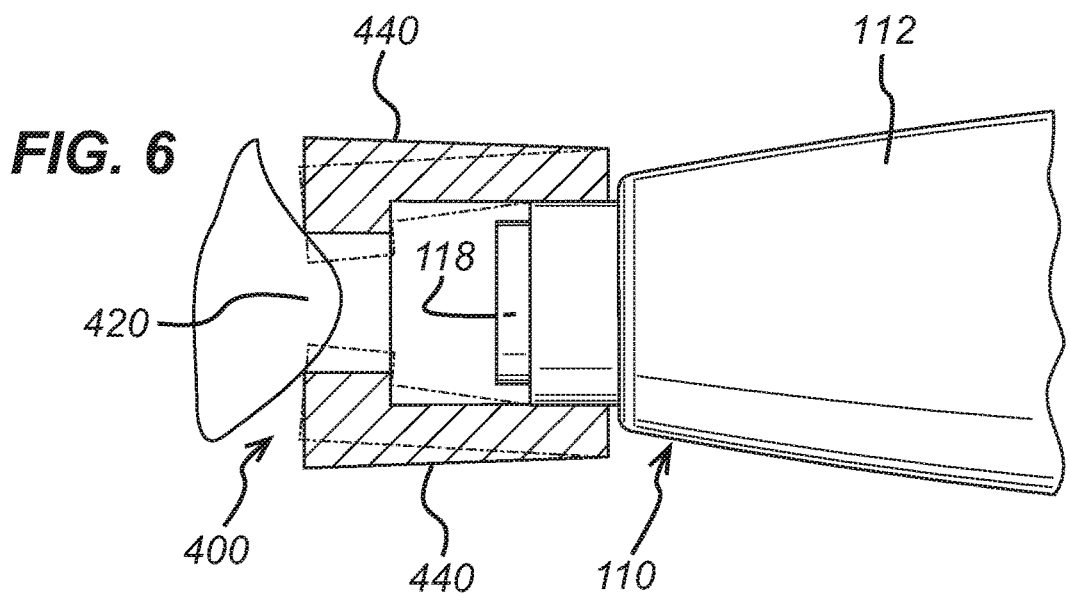
FIG. 6 shows a cross-section view of a guide in accordance with the present invention.

FIG. 6 shows an alternative embodiment of the guide in which the second open end 410 comprises two arms 440. The arms 440 are resiliently biased towards the centre of the guide such that they act to pinch tissue between them when they are placed on the user's skin. This secures the guide 400 to the user's skin and ensures it cannot shift position as the injection device is advanced through the drive and towards the skin and subsequently operated. In addition, pinching of the skin towards the aperture 118 of the device 110 from which the discharge nozzle extends is desirable when a substance is to be injected subcutaneously.

A kit may be provided which includes the injection device and the guide which is attached to the user prior to injection. Alternatively, the injection device may be supplied with the guide pre-affixed to the distal end.

In use, such an injection device as described above might be used to deliver substances such as: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity. In addition to these substances, any medicament contained within the injection device may also include other substances, such as inactive ingredients, as a skilled person would appreciate.

It will of course be understood by the person skilled in the art that particular substances are efficacious for use in the treatment or prevention of particular conditions, as is well known in the art. For instance, it is known that antiallergics are efficacious for use in the treatment or prevention of allergies; antihistamines are efficacious for use in the treatment or prevention of hay fever; anti-inflammatories are efficacious for use in the treatment or prevention of inflammation; and so on. Accordingly, any selection of one or more substances listed herein or in the claims for use in the treatment or prevention of one or more conditions for which those substance(s) are known to be efficacious is envisaged.

In a particular example, however, golimumab is known to be efficacious for use in the treatment or prevention of one or more of rheumatoid arthritis, psoriatic arthritis, ankylosing spondylitis or ulcerative colitis, or any combination of rheumatoid arthritis, psoriatic arthritis, ankylosing spondylitis and ulcerative colitis, or all of rheumatoid arthritis, psoriatic arthritis, ankylosing spondylitis and ulcerative colitis.

Golimumab may optionally be used in combination with one or more inactive ingredients such as any or all of L-histidine, L-histidine monohydrochloride monohydrate, sorbitol, polysorbate 80, and water. Golimumab may present in a composition in which golimumab is the only active ingredient. For example, golimumab may administered as SIMPONI®.

It will of course be understood that the present invention has been described above purely by way of example and modifications of detail can be made within the scope of the invention.

The invention claimed is:

1. A guide for contacting an injection device with a user, the guide comprising:
   a first component including a first end adapted to engage a housing of the injection device, the first component including at least one ratchet tooth;
   a second component including a second end adapted to engage a surface of the user's skin, wherein the second component is movable with respect to the first component, and wherein the second component comprises an inner surface including a plurality of ratchet teeth disposed in series that engage the at least one ratchet tooth on the first component such that the housing moves towards the user's skin incrementally.

2. The guide of claim 1, wherein the first end is open.

3. The guide of claim 1 or claim 2, wherein the second end is open.

4. The guide of claim 1, wherein the guide is cylindrical.

5. The guide of claim 1, wherein the guide is formed as a frame.

6. The guide of claim 1, wherein the guide is formed with a continuous external surface.

7. The guide of claim 1, wherein the guide comprises at least one stabilising element at the second end which is adapted to project from the guide and stabilise the guide on the skin.

8. The guide of claim 7, wherein the guide comprises three stabilising elements at the second end.

9. A kit comprising the guide of claim 1 and an automatic injection device having a housing.

10. The kit of claim 9, wherein the housing has a distal end and the first end of the guide is adapted to engage the housing at the distal end.

11. The kit of claim 9, wherein the housing has a first diameter and the first end is dimensioned to surround the first diameter.

12. The kit of claim 11, wherein a portion of the housing has a second diameter which is larger than the first diameter and the first end is dimensioned to engage the portion of the housing having a second diameter.

13. The kit of claim 12, wherein the second diameter portion comprises a ridge.

14. The kit of claim 9, wherein the first end is integral to the housing of the injection device.

15. An injection device comprising:
   a housing adapted to receive a syringe having a discharge nozzle, the syringe being moveable in the housing on actuation of the injection device along a longitudinal axis from a retracted position in which the discharge nozzle is contained within the housing and an extended position in which the discharge nozzle of the syringe extends from the housing through an exit aperture at a distal end of the device;
   a sliding component which extends, when in a first position, from the aperture, and is movable towards the housing into a second, retracted, position; and
   a guide for contacting an injection device with a user; the guide comprising:
   a first component including a first end adapted to engage the housing, the first component including at least one ratchet tooth,
   a second component including a second end adapted to engage a surface of the user's skin, wherein the second component is movable with respect to the first component, and wherein the second component includes an inner surface having a plurality of ratchet teeth disposed in series that engage the at least one ratchet tooth on the first component such that the housing moves towards the user's skin incrementally.

16. A device according to claim 15, further comprising:
an actuator; and
a drive adapted to be acted upon by the actuator and in turn act upon the syringe to advance it from its retracted position to its extended position and discharge its contents through the discharge nozzle.

17. A device according to claim 15, wherein the sliding component is part of a locking mechanism moveable from an engaged position, when the sliding component is in its first position, to a disengaged position, when the sliding component is in its second position, and adapted to prevent actuation of the device when it is in its engaged position and permit actuation of the device when it is in its disengaged position.

18. A kit according to any one of claims 9 to 11 or 12 to 14 or an injection device according to any one of claims 15 to 17, wherein the injection device contains a substance selected from the group consisting of:
golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines,
for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

19. A substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines,
for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity,
by delivery of said substance to a human subject using a kit according to any one of claims 9 to 11 or 12 to 14 or an injection device according to any one of claims 15 to 17.

20. An injection device for use in the treatment or prevention rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity,
by delivery of a substance selected from the group consisting of: golimumab, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines,
to a human subject by using the injection device, wherein the injection device is an injection device according to any one of claims 15 to 17 or is comprised in a kit according to any one of claims 9 to 11 or 12 to 14.

* * * * *